US006387544B1

(12) United States Patent
Thompson et al.

(10) Patent No.: US 6,387,544 B1
(45) Date of Patent: May 14, 2002

(54) OLEDS CONTAINING THERMALLY STABLE GLASSY ORGANIC HOLE TRANSPORTING MATERIALS

(75) Inventors: Mark E. Thompson, Anaheim; Loy Douglas, Lakewood, both of CA (US); Stephen R. Forrest, Princeton, NJ (US); Bryan E. Koene, Watertown, MA (US); Diarmuid O'Brien, Princeton, NJ (US)

(73) Assignees: The Trustees of Princeton University, Princeton, NJ (US); The University of Southern California, Los Angeles, CA (US)

(*) Notice: Subject to any disclaimer, the term of this patent is extended or adjusted under 35 U.S.C. 154(b) by 0 days.

(21) Appl. No.: 09/204,386

(22) Filed: Dec. 2, 1998

Related U.S. Application Data

(63) Continuation-in-part of application No. 09/058,305, filed on Apr. 10, 1998, now Pat. No. 6,150,093.

(51) Int. Cl.[7] ............... H05B 33/12; C07D 223/14; C07D 211/42
(52) U.S. Cl. ............ 428/690; 428/917; 313/504; 313/506; 540/576; 540/587; 564/427; 564/428
(58) Field of Search ............... 428/690, 704, 428/917; 313/504, 506; 540/484, 576, 587; 564/426, 427, 428, 429, 431

(56) References Cited

U.S. PATENT DOCUMENTS

| | | | |
|---|---|---|---|
| 4,769,292 A | 9/1988 | Tang et al. | 428/690 |
| 5,061,569 A | 10/1991 | VanSlyke et al. | 428/487 |
| 5,294,869 A | 3/1994 | Tang et al. | 313/504 |
| 5,294,870 A | 3/1994 | Tang et al. | 313/504 |
| 5,409,783 A | 4/1995 | Tang et al. | 428/690 |
| 5,554,220 A | 9/1996 | Forrest et al. | 117/88 |
| 5,703,436 A | 12/1997 | Forrest et al. | 313/506 |
| 5,707,745 A | 1/1998 | Forrest et al. | 428/432 |
| 5,759,444 A | 6/1998 | Enokida et al. | 252/301.16 |
| 5,998,803 A | 12/1999 | Forrest et al. | 257/40 |
| 6,150,043 A | * 11/2000 | Thompson et al. | 428/690 |
| 6,242,115 B1 | * 6/2001 | Thomson et al. | 428/690 |

FOREIGN PATENT DOCUMENTS

| | | |
|---|---|---|
| EP | 0 699 654 | 3/1996 |
| EP | 0 879 868 | 11/1998 |
| JP | 4-78859 | 3/1992 |

OTHER PUBLICATIONS

Forrest, S.R., et al., "Organic Emitters Promise a New Generation of Displays," *Laser Focus World*, Feb. 1995, pp. 99–107.

Han, E., et al., "Scanning Force Microscopy of Organic Thin–Film Amorphous Hole Transport Materials," *J. Appl. Phys.*, vol. 80, pp. 3297–3305, Sep. 15, 1996.

Inada, H., et al., "Photo– and Electro–active Amorphous Molecular Materials: Morphology, Structures, and Hole Transport Properties of Tri(biphenyl–4–yl)amine," *J. Mater. Chem.*, vol. 4, 1994, pp. 171–177. (No Month).

Naito, K., et al., "Molecular Design for Nonpolymeric Organic Dye Glasses with Thermal Stability: Relations Between Thermodynamic Parameters and Amorphous Properties," *J. Phys. Chem.*, vol. 97, 1993, pp. 6240–6248. (No Month).

Noda, T., et al., "A Novel Yellow–emitting Material, 5,5"–bis{4–[bis(4–methylphenyl)amino] phenyl }–2,2':5',2"–Terthiophene, for Organic Electroluminescent Devices," *Appl. Phys. Lett.*, vol. 70, No. 6, pp. 699–701, Feb. 10, 1997.

Noda, T., et al., "5,5"–Bis{4–methylphenyl)amino ]phenyl}–2,2':5',2"–Terthiophene and . . . as a Novel Family of Amorphous Molecular Materials," *Advance Materials*, vol. 9, No. 3, 1997, pp. 239–241. (No Month).

Rommens, J., et al., "Hole Injection into Molecular Dispersions of 5'–[4–[Bis(4–ethylphenyl)amino]phenyl]–. . . –terphenyl –4,4"–diamine," J. Phys. Chem. B, vol. 101, No. 16, 1997, pp. 3081–3086. (No Month).

Salbeck, J., et al., "Low Molecular Organic Glasses for Blue Electroluminescence," *Synthetic Metals*, vol. 91, 1997, pp. 209–215. (No Month).

Shirota, Y., et al., "Starburst Molecules for Amorphous Molecular Materials . . . N–phenylamino]triphenylamme," *Chem. Lett.*, 1989, pp. 1145–1148. (No Month).

Tang, C.W., et al. "Organic Electroluminescent Diodes," *Appl. Phys. Lett.*, vol. 51, No. 12, Sep. 1987, pp. 913–915.

Tokito, S., et al., "High–Temperature Operation of an Electroluminescent Device Fabricated Using a Novel Triphenylamine Derivative," *Appl. Phys. Lett.*, vol. 69, No. 7, pp. 878–880, Aug. 12, 1996.

Van Slyke, S.A., et al., "Organic Electroluminescent Devices with Improved Stability," *Appl. Phys. Lett.*, vol. 69, No. 15, pp. 2160–2162, Oct. 7, 1996.

* cited by examiner

*Primary Examiner*—Marie Yamnitzky
(74) *Attorney, Agent, or Firm*—Kenyon & Kenyon

(57) ABSTRACT

Organic light emitting devices comprising a heterostructure for producing electroluminescence having a hole transporting layer with a glass structure. The hole transporting layer comprises a compound having a symmetric molecular structure. The end groups of the symmetric molecule are hole transporting diaryl amine moieties.

32 Claims, 7 Drawing Sheets

OLEDS CONTAINING THERMALLY STABLE GLASSY ORGANIC HOLE TRANSPORTING MATERIALS

This application is a continuation-in-part of U.S. application Ser. No. 09/058,305 filed Apr. 10, 1998, now U.S. Pat. No. 6,150,093.

GOVERNMENT RIGHTS

This invention was made with Government support under Contract No. F33615-94-1-1414 awarded by DARPA. The government has certain rights in this invention.

FIELD OF INVENTION

The present invention is directed to organic light emitting devices (OLEDs) comprised of glassy organic hole transporting materials comprised of compounds having a symmetric molecular structure, for example, hole transporting materials comprised of thermally stable symmetric derivatives of phenyl or biphenyl diamines. One such biphenyl derivative is fluorene, in which the 2,2'-positions of biphenyl are bridged by a methylene group.

BACKGROUND OF THE INVENTION

Organic light emitting devices (OLEDs) are comprised of several organic layers in which one of the layers is comprised of an organic material that can be made to electroluminescence by applying a voltage across the device. C. W. Tang et al., *Appl. Phys. Lett.* 51, 913 (1987). Certain OLEDs have been shown to have sufficient brightness, range of color and operating lifetimes for use as a practical alternative technology to LCD-based full color flat-panel displays. S. R. Forrest, P. E. Burrows and M. E. Thompson, Laser Focus World, Feburary 1995. Since many of the thin organic films used in such devices are transparent in the visible spectral region, they allow for the realization of a completely new type of display pixel in which red (R), green (G), and blue (B) emitting OLEDs are placed in a vertically stacked geometry to provide a simple fabrication process, a small R-G-B pixel size, and a large fill factor.

A transparent OLED (TOLED), which represents a significant step toward realizing high resolution, independently addressable stacked R-G-B pixels, was reported in U.S. Pat. No. 5,703,436, Forrest et al. This TOLED had greater than 71% transparency when turned off and emitted light from both top and bottom device surfaces with high efficiency (approaching 1% quantum efficiency) when the device was turned on. The TOLED used transparent indium tin oxide (ITO) as the hole-injecting electrode and a Mg—Ag-ITO electrode layer for electron-injection. A device was disclosed in which the ITO side of the Mg—Ag-ITO electrode layer was used as a hole-injecting contact for a second, different color-emitting OLED stacked on top of the TOLED. Each layer in the stacked OLED (SOLED) was independently addressable and emitted its own characteristic color, red or blue. This colored emission could be transmitted through the adjacently stacked transparent, independently addressable, organic layer, the transparent contacts and the glass substrate, thus allowing the device to emit any color that could be produced by varying the relative output of the red and blue color-emitting layers.

U.S. Pat. No. 5,703,745, Forrest et al, disclosed an integrated SOLED for which both intensity and color could be independently varied and controlled with external power supplies in a color tunable display device. U.S. Pat. No. 5,703,745, thus, illustrates a principle for achieving integrated, full color pixels that provide high image resolution, which is made possible by the compact pixel size. Furthermore, relatively low cost fabrication techniques, as compared with prior art methods, may be utilized for making such devices.

Such devices whose structure is based upon the use of layers of organic optoelectronic materials generally rely on a common mechanism leading to optical emission. Typically, this mechanism is based upon the radiative recombination of a trapped charge. Specifically, OLEDs are comprised of at least two thin organic layers between an anode and a cathode. The material of one of these layers is specifically chosen based on the material's ability to transport holes, a "hole transporting layer" (HTL), and the material of the other layer is specifically selected according to its ability to transport electrons, an "electron transporting layer" (ETL). With such a construction, the device can be viewed as a diode with a forward bias when the potential applied to the anode is higher than the potential applied to the cathode. Under these bias conditions, the anode injects holes (positive charge carriers) into the HTL, while the cathode injects electrons into the ETL. The portion of the luminescent medium adjacent to the anode thus forms a hole injecting and transporting zone while the portion of the luminescent medium adjacent to the cathode forms an electron injecting and transporting zone. The injected holes and electrons each migrate toward the oppositely charged electrode. When an electron and hole localize on the same molecule, a Frenkel exciton is formed. These excitons are trapped in the material which has the lowest energy. Recombination of the short-lived excitons may be visualized as an electron dropping from its conduction potential to a valence band, with relaxation occurring, under certain conditions, preferentially via a photoemissive mechanism.

The materials that function as the ETL or HTL of an OLED may also serve as the medium in which exciton formation and electroluminescent emission occur. Such OLEDs are referred to as having a "single heterostructure" (SH). Alternatively, the electroluminescent material may be present in a separate emissive layer between the HTL and the ETL in what is referred to as a "double heterostructure" (DH).

In a single heterostructure OLED, either holes are injected from the HTL into the ETL where they combine with electrons to form excitons, or electrons are injected from the ETL into the HTL where they combine with holes to form excitons. Because excitons are trapped in the material having the lowest energy gap, and commonly used ETL materials generally have smaller energy gaps than commonly used HTL materials, the emissive layer of a single heterostructure device is typically the ETL. In such an OLED, the materials used for the ETL and HTL should be chosen such that holes can be injected efficiently from the HTL into the ETL. Also, the best OLEDs are believed to have good energy level alignment between the highest occupied molecular orbital (HOMO) levels of the HTL and ETL materials.

In a double hetrostructure OLED, holes are injected from the HTL and electrons are injected from the ETL into the separate emissive layer, where the holes and electrons combine to form excitons.

Various compounds have been used as HTL materials or ETL materials. HTL materials mostly consist of triaryl amines in various forms which show high hole mobilities ($\sim 10^{-3}$ cm$^2$/Vs). There is somewhat more variety in the ETLs used in OLEDs. Aluminum tris(8-hydroxyquinolate) (Alq$_3$) is the most common ETL material, and others include oxidiazol, triazol, and triazine.

A well documented cause of OLED failure is thermally induced deformation of the organic layers (e.g. melting, crystal formation, thermal expansion, etc.). This failure mode can be seen in the studies that have been carried out with hole transporting materials, K. Naito and A. Miura, J. Phys. Chem. (1993), 97, 6240–6248; S. Tokito, H. Tanaka, A. Okada and Y. Taga. Appl. Phys. Lett. (1996), 69, (7), 878–880; Y. Shirota, T Kobata and N. Noma, Chem. Lett. (1989), 1145–1148; T. Noda, I. Imae, N. Noma and Y. Shirota, Adv. Mater. (1997), 9, No. 3; E. Han, L. Do, M. Fujihira, H. Inada and Y. Shirota, J. Appl. Phys. (1996), 80, (6) 3297–701; T. Noda, H. Ogawa, N. Noma and Y. Shirota, Appl. Phys. Lett. (1997), 70, (6), 699–701; S. Van Slyke, C. Chen and C. Tang, Appl. Phys. Lett. (1996), 69, 15, 2160–2162; and U.S. Pat. No. 5,061,569.

Organic materials that are present as a glass, as opposed to a crystalline or polycrystalline form, are desirable for use in the organic layers of an OLED, since glasses are capable of providing higher transparency as well as producing superior overall charge carrier characteristics as compared with the polycrystalline materials that are typically produced when thin films of the crystalline form of the materials are prepared. However, thermally induced deformation of the organic layers may lead to catastrophic and irreversible failure of the OLED if a glassy organic layer is heated above its $T_g$. In addition, thermally induced deformation of a glassy organic layer may occur at temperatures lower than $T_g$, and the rate of such deformation may be dependent on the difference between the temperature at which the deformation occurs and $T_g$. Consequently, the lifetime of an OLED may be dependent on the $T_g$ of the organic layers even if the device is not heated above $T_g$. As a result, there is a need for organic materials having a high $T_g$ that can be used in the organic layers of an OLED.

A common hole transporting material used in the HTL of OLEDs is a biphenyl bridged diamine, N,N'-diphenyl-N,N'-bis(3-methylphenyl)-1,1-biphenyl-4,4'-diamine (TPD) having the chemical structure:

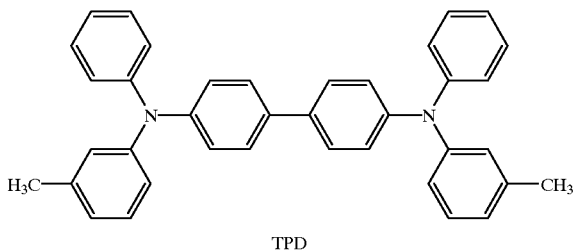

TPD

This material has a good hole mobility and efficiently transfers holes to aluminum tris (8-hydroxyquinoline) in a simple single heterostructure OLED. However, TPD has a melting point of 167° C. and a glass transition temperature of 65° C. If a device prepared with TPD is heated above 65° C., the glass transition temperature, catastrophic and irreversible failure results. In order to increase the glass transition temperature of the HTL, several groups have explored different modifications to the basic structure of TPD, Naito et al.; Tokito et al.; Shirota et al.; Noda et al (Adv. Mater.); Han et al.; Noda et al. (Appl. Phys. Lett.); Van Slyke et al.; and U.S. Pat. No. 5,061,569. While these studies have led to materials with $T_g$ values as high as 150° C., they have not led to an understanding of why certain structural modifications increase $T_g$, while other modifications may not affect $T_g$ at all or may even lower $T_g$. Still other modifications may produce a material not having a glass transition temperature at all or a material not having the combination of properties that is suitable for use in an HTL. For example, replacing the amine groups of TPD with carbazole groups to produce 4,4'-di(N-carbazolo)diphenyl (CBP), having the chemical structure:

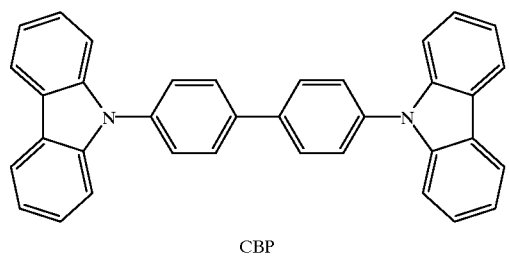

CBP increases the melting point to 285° C. However, the material shows no glass transition. Further changes in the basic structure of TPD can increase the $T_g$ value even higher, but the materials often have poorer hole transporting properties than TPD, i.e. OLEDs made with these high temperature materials give poor device properties in OLEDs compared to TPD.

U.S. Pat. No. 5,061,569 discloses hole transporting materials comprised of at least two tertiary amine moieties and further including an aromatic moiety containing at least two fused aromatic rings attached to the tertiary amine nitrogen atoms. Out of the large number of compounds encompassed by the broadly disclosed class of compounds recited, U.S. Pat. No. 5,061,569 fails to disclose how to select those compounds which have a high glass transition temperature. For example, the naphthyl derivatives do make stable glasses. One such molecule is 4,4'-bis[N-(1-naphthyl)-N-phenyl-amino]biphenyl (α-NPD), having the chemical structure:

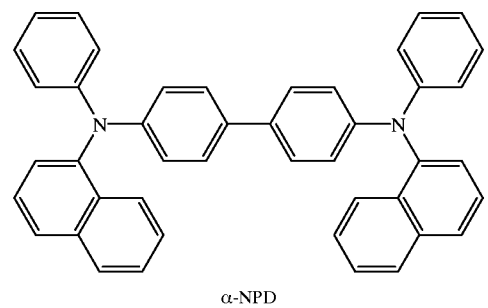

α-NPD

The present inventors' measurements show that α-NPD has a $T_g$ of 100–105° C., which is substantially higher than the $T_g$ of 65° C. of TPD. This material has excellent hole conduction properties, and the $T_g$ of 100–105° C. is higher than the $T_g$ of TPD of about 65° C. OLEDs prepared with NPD have electrical properties very similar to those prepared with TPD. However, 4,4'-bis[N-(2-naphthyl)-N-phenyl-amino]biphenyl (β-NPD), having the structure:

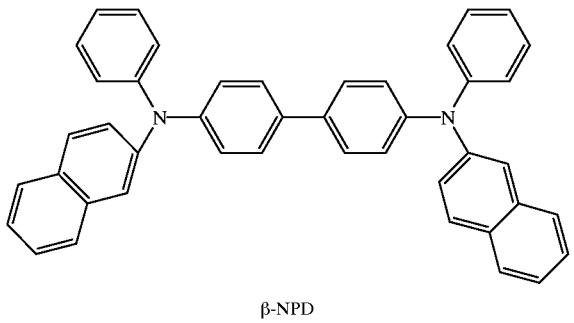

β-NPD has been generally understood to have a $T_g$ which is substantially lower than α-derivative. Apparently because of this purportedly low and anomalous difference between $T_g$ of the α- β-derivatives, there had been no known reports of using the β-derivative as the hole transporting material of an OLED.

It would be desirable if OLED's could be fabricated from glassy charge carrier materials having improved temperature stability, while still providing luminescent characteristics comparable to prior art compounds. As used herein, the term "charge carrier layer" may refer to the hole transporting layer, the electron transporting layer or the separate emissive layer of an OLED having a double heterostructure. In addition, it would be useful to have a method for selecting and preparing such glassy charge carrier materials having improved temperature stability, as characterized, in particular, by glassy charge carrier materials having a high glass transition temperature.

In addition, there is a general inverse correlation between the $T_g$ and the hole transporting properties of a material, i.e., materials having a high $T_g$ generally have poor hole transporting properties. Using an HTL with good hole transporting properties leads to an OLED having desirable properties such as higher quantum efficiency, lower resistance across the OLED, higher power quantum efficiency, and higher luminance. There is therefore a need for a HTL having a high hole mobility and a high glass transition temperature.

SUMMARY OF THE INVENTION

The present invention is directed to organic light emitting devices comprising a heterostructure for producing electroluminescence having a hole transporting layer with a glass structure. The hole transporting layer comprises a compound having a symmetric molecular structure. The end groups of the symmetric molecule are hole transporting diaryl amine moieties.

DETAILED DESCRIPTION

Figure 1:
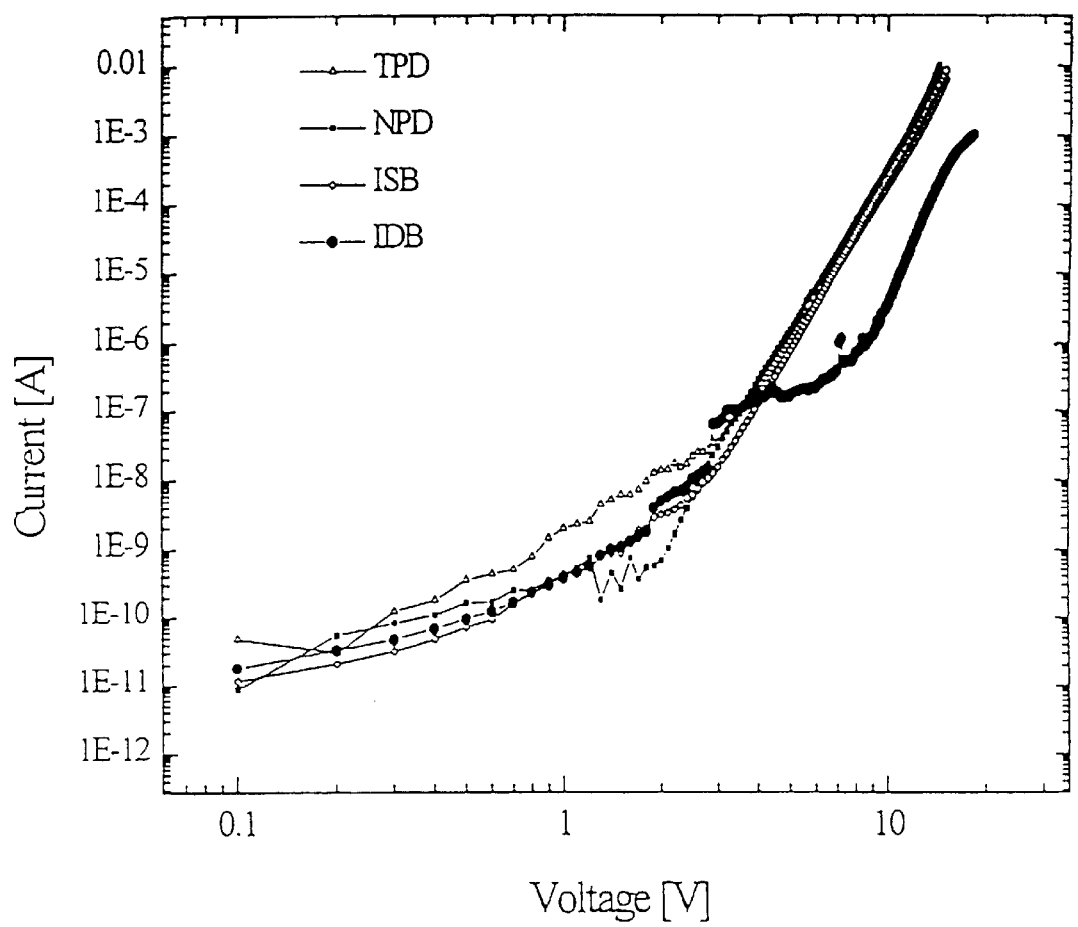
FIG. 1 shows a plot of current v. voltage for an embodiment of the present invention.

The present invention will now be described in detail for specific preferred embodiments of the invention, it being understood that these embodiments are intended only as illustrative examples and the invention is not to be limited thereto.

The present invention is directed to organic light emitting devices comprising a heterostructure for producing electroluminescence having a hole transporting layer with a glass structure. The hole transporting layer comprises a compound having a symmetric molecular structure. The end groups of the symmetric molecule are hole transporting diaryl amine moieties. The diaryl amine moieties may contain an unsaturated linkage between the two arenes or the diaryl amine moiety may be an asymmetrically substituted diaryl amine group.

The term "unsaturated linkage" as used herein refers to a linkage in which there is at least one double bond. The term "arene" as used herein refers to a hydrocarbon containing at least one aromatic. The term "symmetric" as used herein refers to a molecule or substituent group having a point about which the molecule or substituent group is symmetric. As used herein, the term "charge carrier layer" may refer to a "hole transporting layer" (HTL,) an "electron transporting layer" (ETL) or, for an OLED having a double heterostructure (DH), a "separate emissive layer."

The term "hole transporting moiety" as used herein, refers to a group which, when present in a material contained in a layer of an OLED, causes the material to provide electrical conduction through the layer, when a voltage is applied, predominantly by the conduction of holes. The term "electron transporting moiety" as used herein, refers to a group which, when present in a material contained in a layer of an OLED, causes the material to provide electrical conduction through the layer, when a voltage is applied, predominantly by the conduction of electrons. The term "hole transporting amine moiety" as used herein, refers to an amine group that is a hole transporting moiety. Such hole transporting amine moieties are typically comprised of nitrogen atoms that are directly bonded to at least two phenyl groups, wherein the two phenyl groups may be joined so as to form a heterocyclic ring including the nitrogen, for example, a carbazole group, or the two phenyl groups may be nattached to each other. Each phenyl group may itself be fused with one or more phenyl groups, being bonded to the nitrogen atom, for example, either as a 1-naphthyl group or as a 2-naphthyl group.

While not intending to be limited by any particular theory or mechanism for explaining exactly how or why such materials have good hole conducting properties, the inventors' examination of electronic structure by semi-empirical theoretical methods shows that a molecule having end groups that are hole transporting moieties having an unsaturated linkage between two arenes has holes delocalized onto the end groups. One such molecule is 4,4'-(N,N'-bisiminostilbene)biphenyl (ISB). By way of contrast, the normal situation in amines such as TPD and NPD is for the nitrogen lone pair to be conjugated through the biphenyl group, such that the hole is delocalized predominantly onto the biphenyl group. The importance of the unsaturated linkage can be shown by examining 4,4'-(N,N'-iminodibenzyl)biphenyl (IDB), which has the same structure as ISB, except that the IDB has a saturated linkage between the amino phenyl groups, while that of ISB is unsaturated. The inventors' analysis shows that IDB has a nitrogen lone pair conjugated through the biphenyl group, whereas ISB has the nitrogen lone pair coupled to the stilbene group, not the biphenyl. To the extent that the hole is delocalized, it is spread onto the stilbene group. This delocalization helps keep the hole on the exterior of the ISB molecule and not on the biphenyl, where it would b,e shielded from adjacent molecules. Keeping the hole on the exterior of the molecule gives it more contact with adjacent molecules and increases the rate of hole transfer to adjacent molecules, which results in good hole conducting properties.

Moreover, the inventors' analysis shows that substitutions may be made to molecules having end groups that have an unsaturated linkage between two arenes, and the holes would still be delocalized on the ends or periphery of the molecule rather than the center.

In particular, the present invention includes symmetric compounds having a biphenyl bridge, as represented by formula (I):

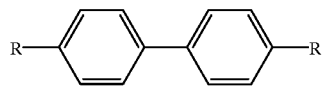

(I)

where R is a hole transporting amine moiety having an unsaturated linkage between two arenes. The molecule represented by formula (I) is symmetric because there is a point in the center of the biphenyl bridge between the two R-groups about which the molecule is symmetric. The term "symmetric" as used herein requires that atoms are on either side of the point of symmetry have the same sequence of bonding between the atoms, i.e., the R-groups must have identical atoms bonded in an identical sequence, but allows for differences in the positions of atoms due to the twisting of bonds.

The present invention also includes symmetric compounds having a phenyl bridge, as represented by formula (II):

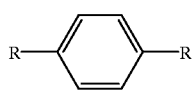

(II)

wherein R has the same meaning as above.

An example of an R-group that is a hole transporting amine moiety having an unsaturated linkage between two arenes is represented by the formula (III):

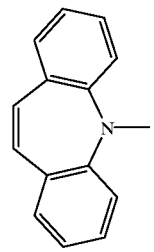

(III)

where the two phenyl groups are the arenes, and the ethenyl group is the unsaturated linkage between the two arenes.

Using the R-group of formula (III) in the molecule of formula (I), the present invention therefore includes ISB, represented by the formula (IV):

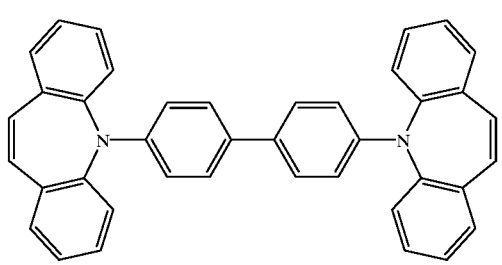

(IV)

ISB

The ethenyl groups of ISB may be substituted while still maintaining the unsaturated linkage between the two arenes. For example, the unsaturated linkage may, in fact, be provided by a phenylene group, resulting in a molecule having a structure as represented by formula (V):

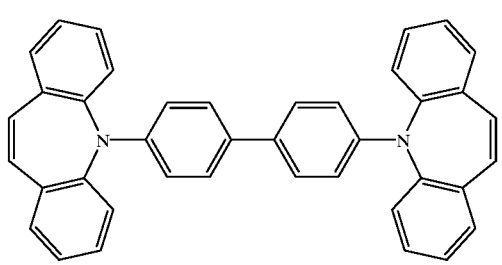

(V)

Alternatively, the ethenyl groups of ISB may be substituted so as to result in a molecule having a structure as represented by formula (VI):

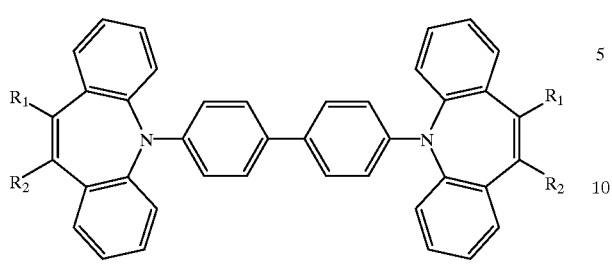

(VI)

where $R_1$ and $R_2$ are selected from the group consisting of: alkyl, phenyl, substituted alkyl, and substituted phenyl groups. $R_1$ may be the same as $R_2$, or may be different.

The substitutions leading to the molecules of formulae (V) and (VI) are expected to assist in shifting the hole delocalization to the ends of the molecule. In addition, the substitutions increase the molecular weight of the molecule and may lead to a higher $T_g$.

In a conventional single heterostructure OLED, the emissive material is the ETL, and the HTL must have an absorption energy higher than that of the ETL. As a result, it is preferable that substitutional made to ISB do not lead to significant shifts in the electronic spectrum if the resultant molecule is to be used in a single heterostructure OLED having an emissive ETL.

To provide a contrast to ISB, a molecule having an R-group that is a hole transporting amine moiety having a saturated linkage between two arenes may be used. Such an R-group is represented by the formula (VII):

(VII)

Using the R-group of formula (VII) in the molecule of formula (I) results in 4,4'-(N,N'-aminodibenzyl)biphenyl (IDB), as represented by the formula (VIII):

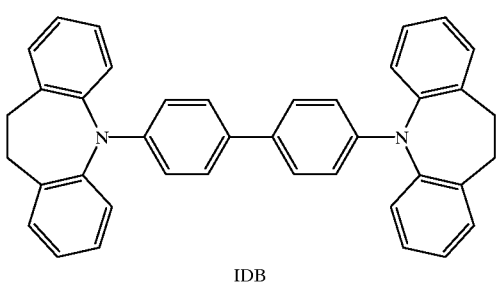

(VIII)

IDB

The thermal and other physical properties of ISB and IDB, as well as those of their phenylene bridged analogs, are given in Table 1:

TABLE 1

Physical data for ISB, IDB and their phenyl bridged analogs.

| compound | melting point (° C.) | $T_g$(° C.) | $\lambda_{max}$ abs. (nm) | $\lambda_{max}$ PL (nm) |
|---|---|---|---|---|
| ISB | 317 | 110 | 300, 340 | 530 |
| IDB | — | 117 | 320 | 402 |
| (structure) | — | 73 | 315 | 368 |
| (structure) | 310 | 110 | 290, 340 | 444, 488 |

The $T_g$ of both ISB (110° C.) and IDB (117° C.) are significantly higher than that of HTL materials conventionally used in OLEDs, such as TPD (65° C.) and NPD (105° C.), which are materials conventionally used in OLEDs. As a result, OLEDs using ISB or IDB as an HTL may be operated at a higher temperature than OLEDs using TPD or NPD, and are expected to have a longer lifetime when operated at the same temperature.

As discussed in greater detail below, two different types of OLEDS were fabricated using ISB and IDB as HTL materials. Similar OLEDs were also fabricated using TPD and NPD as HTL materials. Both types of OLED start with an ITO coated substrate as an anode and use a Mg—Ag cathode. The simplest OLED structure examined was ITO/ HTL/Alq$_3$/Mg—Ag. A slightly more complicated structure uses a copper phthalocyanine, CuPc, hole injector, i.e. ITO/CuPc/HTL/Alq$_3$/Mg—Ag. The use of a CuPc hole injector, such as disclosed in copending application Ser. No. 08/865,491, can provide improved quantum yields. As illustrated in Table 2, it vias observed for both types of OLED that OLEDS using ISB as the HTL have superior performance to those using IDB, and that OLEDs using ISB have performance comparable to that of OLEDs using NPD:

modified by the addition of a methylene group connecting the 2,2' positions of the biphenyl. The resulting fluorene bridged structure is represented by formula (IX):

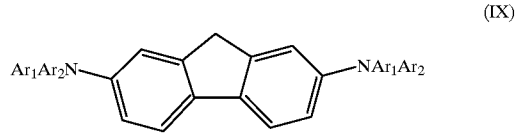

(IX)

wherein $Ar_1$ and $Ar_2$ are substituted or unsubstituted arene moieties. The arene moieties may be phenyl groups or phenyl groups fused with one or more additional phenyl groups resulting in, for example, naphthalene, phenanthrene or anthracene. The arene moieties may be substituted with one or more alkyl, alkoxy, alkylene, or halogen groups. It is advantageous that $Ar_1$ and $Ar_2$ are different, so as to form an asymmetrically substituted diaryl amine group, as this tends to result in a material with a higher $T_g$.

Examples of diaryl amines, —$NAr_1Ar_2$, useful as hole transporting moieties are represented by the formulas:

TABLE 2

| | Quantum Efficiency with CuPc layer | Quantum Efficiency without CuPc layer | V @ 0.1 mA with CuPc layer | V @ 0.1 mA without CuPc layer | Power Q.E. without CuPc layer at 200 cd/m$^2$ (W/W) | Power Q.E. without CuPc layer at 200 cd/m$^2$ (W/W) | Luminance @ 5 mA for 1 mm dot with CuPc layer | Luminance @ 5 mA for mm dot without CuPc layer |
|---|---|---|---|---|---|---|---|---|
| ISB | 0.58% | 0.62% | 7.5 V | 9.0 V | 0.174 | 0.156 | 8460 | 8930 |
| IDB | 0.30% | 0.15% | 9.5 V | 12.9 V | 0.071 | 0.025 | 1510 @ 1 mA | 470 @ 1 mA |
| α-NPD | 0.85% | 0.88% | 7.3 V | 8.65 V | 0.285 | 0.251 | 12550 | 12925 |
| TPD | 0.78% | 0.93% | 8.25 V | 9.20 V | 0.230 | 0.250 | 11280 | 13865 |

The quantum yields, turn-on voltages and power efficiencies of the ISB based devices are very good and the higher $T_g$ suggests that the ISB based OLEDs would have significantly improved lifetime, and can be operated at higher temperatures, than NPD and TPD based OLEDs. The similarity of the TPD, NPD and ISB OLED device properties can also be seen in FIGS. 1 and 2. The current-voltage plots of OLEDs made TPD, NPD and ISB are nearly indistinguishable, while IDB is poorer.

Table 2 also shows that OLEDs using ISB as the HTL have significantly better properties than OLEDs using IDB as the HTL in several respects. The ISB based OLEDs have a higher quantum efficiency, a require a lower voltage to achieve the same current, and have a higher luminance at the same current. ISB and IDB are both symmetric molecules having a high $T_g$. The only structural difference between ISB and IDB is that ISB has an unsaturated linkage between the amino phenyl groups, while that of IDB is saturated. This difference in the properties of OLEDs using ISB as opposed to IDB is consistent with ISB having better hole conducting properties than IDB. While the $T_g$ of IDB is slightly higher than that of ISB, this higher $T_g$ alone is not expected to alter the OLED properties by the amount observed here.

The present invention also includes symmetric compounds having a fluorene bridge. The biphenyl bridge can be

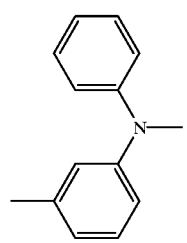

(X)

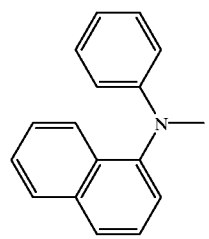

(XI)

(XII)

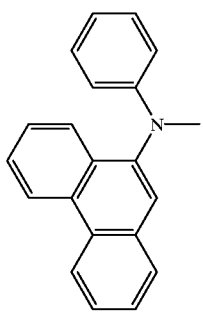

(XIII)

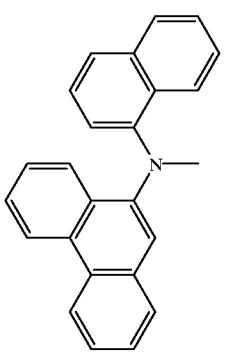

Using the diaryl amines of the formulas (X), (XI), (XII), and (XIII) in the molecule of the formula (IX) results in TPF, NPF, APF, and ANF, as represented by the formulas (XIV), (XV), (XVI), and (XVII), respectively:

(XIV)

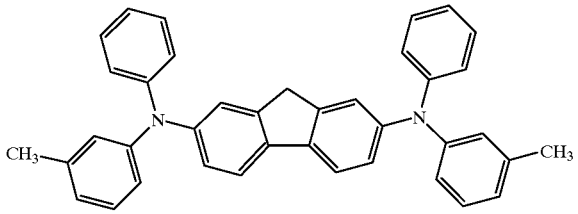

TPF (XV)

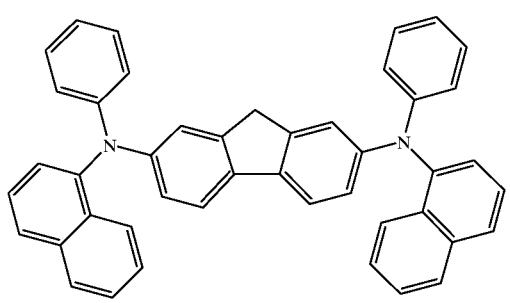

NPF (XVI)

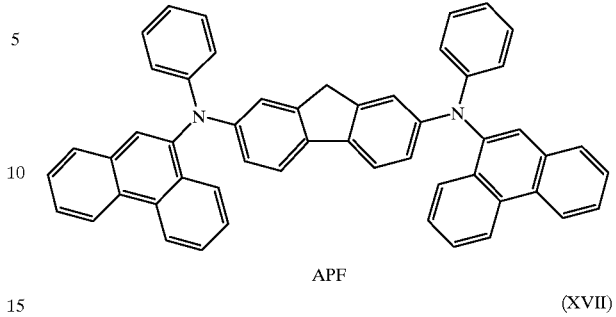

APF (XVII)

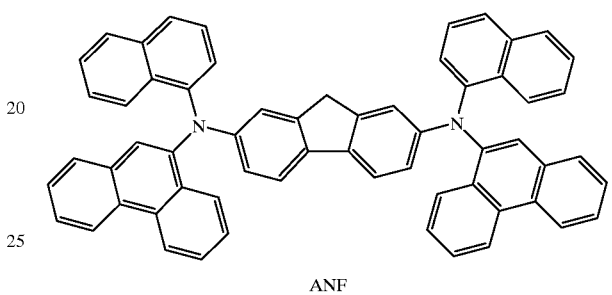

ANF

The present invention also includes symmetric compounds having a fluorene bridge, as represented by the formula (XVIII):

(XVIII)

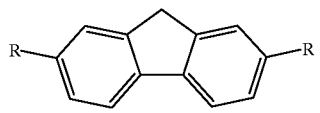

wherein the R-group has the same meaning as above. Compounds represented by the formula (XVIII) are a variation of the general formula (IX) in which the two arene moieties of the diaryl amine are connected by an unsaturated linkage.

Using the R-group of formula (III) in the molecule of formula (XVIII), the present invention therefore includes ISF, represented by the formula (XIX):

(XIX)

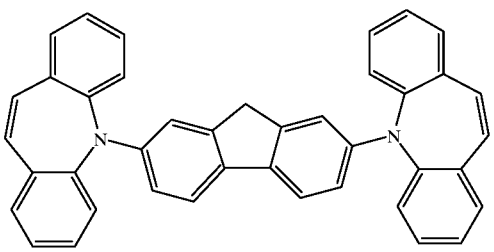

ISF

The ethenyl groups of ISF may be substituted while still maintaining the unsaturated linkage between the two arenes. For example, the unsaturated linkage may, in fact, be provided by a phenylene group, resulting in a molecule having a structure as represented by formula (XX):

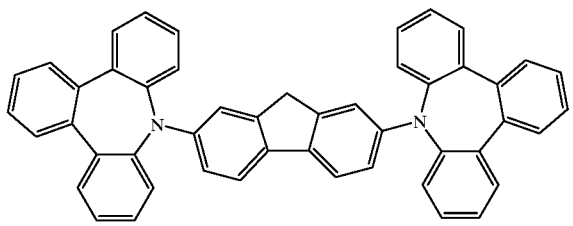

(XX)

Alternatively, the ethenyl groups of ISB may be substituted so as to result in a molecule having a structure as represented by formula (XXI):

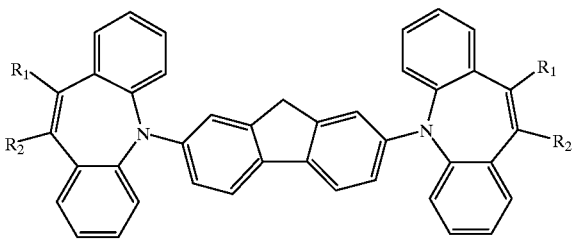

(XXI)

where $R_1$ and $R_2$ are selected from the group consisting of: alkyl, phenyl, substituted alkyl, and substituted phenyl groups. $R_1$ may be the same as $R_2$, or may be different.

The substitutions leading to the molecules of formulae (XX) and (XXI) are expected to assist in shifting the hole delocalization to the ends of the molecule. In addition, the substitutions increase the molecular weight of the molecule and may lead to a higher $T_g$.

The methylene group of the fluorene bridge is responsible for an increase in thermal stability as well as tuning the electronic properties. This methylene holds the phenyl rings of the fluorene in a coplanar position prohibiting rotation that is present in the normal biphenyl and lowering the degrees of freedom. The loss in the degrees of freedom inhibits molecular ordering in the overall molecular structure. This increases the ability of a material to form stable amorphous films as seen in the increase in the glass transition temperature. Table 3 shows the $T_g$ of some of these fluorene-based materials as well as their biphenyl analogues.

TABLE 3

| Fluorene bridged | | Biphenyl analog | |
| --- | --- | --- | --- |
| Material | $T_g$ (° C.) | Material | $T_g$ (° C.) |
| TPF | 78 | TPB | 60 |
| NPF | 118 | NPB | 95 |
| ISF | 161 | ISB | 110 |
| APF | 164 | | 152 |
| ANF | 220 | | 190 |

Figure 7:
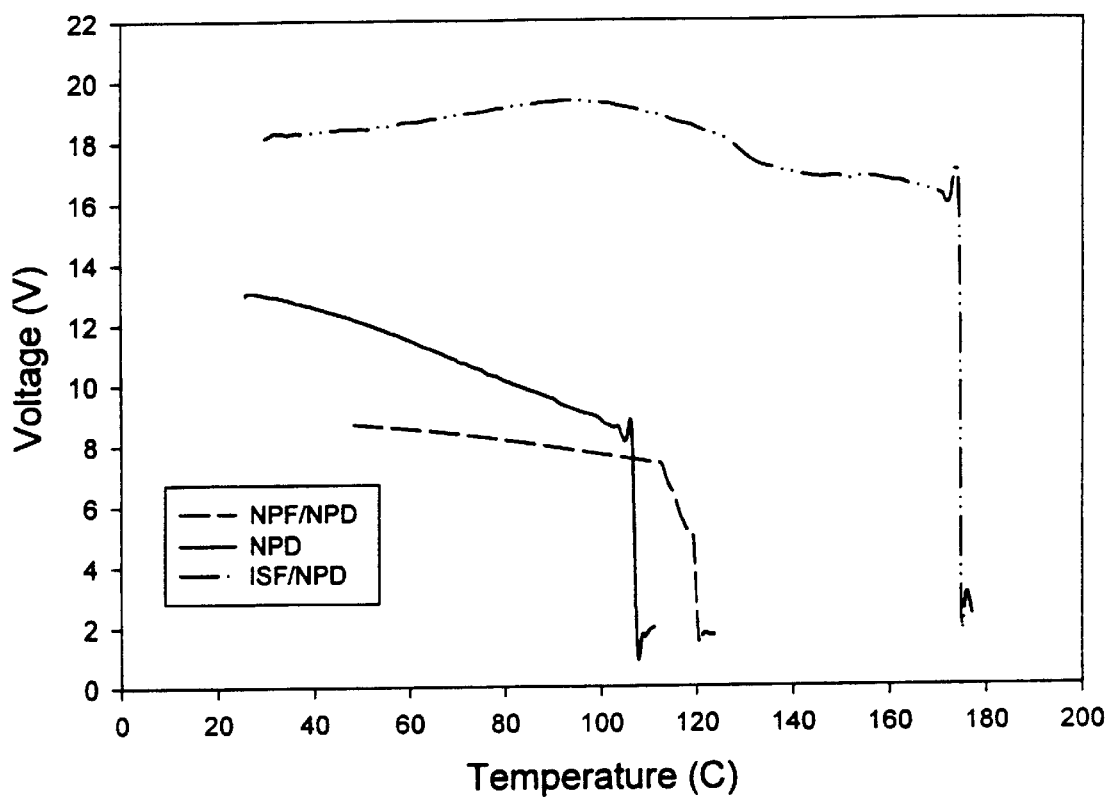
FIG. 7 shows plots of voltage v. temperature for OLEDs having an HTL comprised of NPF/NPD, ISF/NPD or NPD.

In all cases the fluorene bridged materials show remarkably improved thermal stability over their biphenyl analogs. This improvement is most notable for ISF, which shows a 51° C. improvement in $T_g$ over ISB. As a result of the improved $T_g$ for the fluorene bridged materials, OLEDs using a fluorene bridged material as the HTL may be operated at a higher temperature and are expected to have a longer lifetime at the same temperature than OLEDs using conventionally used HTLs. The improved thermal stability is can be seen in FIG. 7. The temperature-voltage plot shows that the temperature at which OLEDs constructed with ISF fail (170° C.) is slightly higher than $T_g$.

Electrochemistry, also used to characterize these materials, can give a good indication of the electrical properties of the material. Hole transporting materials should be easily oxidized, as seen in a low oxidation potential, and this oxidation should be completely reversible. Table 4 shows the first oxidation potential of the fluorene-based material compared to that of their biphenyl analogs.

TABLE 4

| Material Acronym | 1st Oxidation Potential (eV) vs. Ag/AgCl | 1st Oxidation Potential (eV) of biphenyl analog vs Ag/AgCl |
| --- | --- | --- |
| TPF | 0.626 | 0.733 |
| NPF | 0.658 | 0.767 |
| ISF | 0.516 | 0.699 |

The fluorene-based materials are shown to have lower oxidation potentials than their biphenyl analogs. This may be attributed to the planarization of the phenyl rings in the bridging fluorene, which facilitates removal of an electron from the HOMO. This oxidation is completely reversible.

The fluorene based materials have a very small shift in their fluorescence/emission spectra compared to their biphenyl analogs, as shown in Table 5.

TABLE 5

| Material Acronym | Absorption/Emission (nm) | Absorption/Emission (nm) of biphenyl analog |
| --- | --- | --- |
| TPF | 340/398 | 315, 355/396 |
| NPF | 360/470 | 270, 340/450 |
| ISF | 295/520 | 300/530 |

From the data above, it appears that the methylene of the fluorene bridge does not have a great effect on the electronic spectra.

The OLEDs of the present invention are comprised of a heterostructure for producing electroluminescence which may be fabricated as a single heterostructure or as a double heterostructure. As used herein, the term "heterostructure for producing electroluminescence" refers to a heterostructure that includes for a single heterostructure, for example, a substrate, a hole injecting anode layer in contact with the substrate, a HTL in contact with the anode layer, an ETL in contact with the HTL, and an electrode injecting cathode layer in contact with the ETL. If the cathode layer is a metal cathode layer of Mg:Ag, then a metal protective layer, for example, made of a layer of Ag for protecting the Mg:Ag cathode layer from atmospheric oxidation, may also be present.

The heterostructure for producing electroluminescence may typically include a protection layer and/or an injection enhancement layer between the anode layer and the HTL or the cathode layer and the ETL. The protection layer serves to protect the underlying organic layers from damage during deposition of an ITO layer, for example. An injection enhancement layer serves to enhance injection of holes from the anode into the adjacent HTL, such as disclosed in copending Ser. No. 08/865,491 (now U.S. Pat. No. 5,998,803), for example, or to enhance injection of electrons from the cathode into the adjacent ETL, such as disclosed in copending application Ser. No. 08/964,863, and copending application Ser. No. 09/054,707 entitled "Highly Transparent Non-Metalic Cathodes," (filed Apr. 3, 1998), for example.

In the preferred embodiments of the present invention, instead of having the hole injecting layer between the anode and the HTL, it has been found preferable to have the HTL layer comprising the novel materials of the subject invention in direct contact with the anode layer and a hole injecting layer present as an intermediate layer between the HTL and ETL. This intermediate hole injecting layer helps to provide improved energy matching for injection of holes into the ETL. A material that is typically used as the hole transporting layer, NPD, may be selected as a representative example of the intermediate hole injecting layer. The present invention is, thus, further directed to an organic light emitting device comprising in sequence, an anode, a hole transporting layer, a hole injecting layer, an electron transporting layer and a cathode. Additional layers may also be present within this sequence of layers.

If a double heterostructure is used to produce electroluminescence, a separate emissive layer is included between the HTL and the ETL. The term "emissive layer" as used herein may refer either to the emissive electron transporting layer or emissive hole transporting layer of a single heterostructure or the separate emissive layer of a double heterostructure. The emissive layer of a double heterostructure is referred to as a "separate" emissive layer so as to distinguish it from the ETL of a single heterostructure, which may also be an emissive layer. The materials, methods and apparatus for preparing the organic thin films of a single or double heterostructure are disclosed, for example, in U.S. Pat. No. 5,554,220, which is incorporated herein in its entirety by reference.

Alternatively, the heterostructure for producing electroluminescence may have an inverted (IOLED) structure in which the sequence of layers deposited on the substrate is inverted, that is, an electron injecting cathode layer is in direct contact with the substrate, an electron transporting layer is in contact with the cathode layer, a hole transporting layer is in contact with the electron transporting layer, and a hole injecting anode layer is in contact with the hole transporting layer.

If the heterostructure for producing electroluminescence is included as part of a stacked OLED (SOLED), one or both of the electrodes of an individual heterostructure may be in contact with an electrode of an adjacent heterostructure. Alternatively, dependent on the circuitry used to drive the SOLED, an insulating layer may be provided between adjacent electrodes of two of the OLEDs in the stack.

The single or double heterostructures as referred to herein are intended solely as examples for showing how an OLED embodying the present invention may be fabricated without in any way intending the invention to be limited to the particular materials or sequence for making the layers shown. For example, a single heterostructure typically includes a substrate which may be opaque or transparent, rigid or flexible, and/or plastic, metal or glass; a first electrode, which is typically a high work function, hole-injecting anode layer, for example, an indium tin oxide (ITO) anode layer; a hole transporting layer; an electron transporting layer; and a second electrode layer, for example, a low work function, electron-injecting, metal cathode layer of a magnesium-silver alloy, (Mg:Ag) or of a lithium-aluminum alloy, (Li:Al).

Materials that may be used as the substrate in a representative embodiment of the present invention include, in particular, glass, transparent polymer such as polyester, sapphire or quartz, or substantially any other material that may be used as the substrate of an OLED.

Materials that may be used as the hole-injecting anode layer in a representative embodiment of the present invention include, in particular, ITO, Zn—In—$SnO_2$ or $SbO_2$, or substantially any other material that may be used as the hole-injecting anode layer of an OLED.

In addition to the materials as disclosed herein for use in the HTL or in the ETL, other materials that may be used in the HTL in a representative embodiment of the present invention include, in particular, N,N'-diphenyl-N,N'-bis(3-methylphenyl)1-1'biphenyl-4,4'diamine (TPD), 4,4'-bis[N-(1-naphthyl)-N-phenyl-amino]biphenyl (α-NPD) or 4,4'-bis [N-(2-naphthyl)-N-phenyl-amino]biphenyl (β-NPD). Other materials that may be used as the ETL include, in particular, aluminum tris(8-hydroxyquinolate) ($Alq_3$), a carbazole, an oxadiazole, a triazole, a thiophene or oligothiophene group. Other materials that may be used as the separate emissive layer, if present, include, in particular, dye-doped $Alq_3$, or substantially any other material that may be used as the separate emissive layer of an OLED.

Materials that may be used as the electron-injecting, metal cathode layer in a representative embodiment of the present invention include, in particular, Mg—Ag, Li—Ag or Ca, or a non-metallic material such as ITO, such as disclosed in copending Ser. No. 08/964,863, or substantially any other material that may be used as the cathode layer of an OLED.

The insulating layer, if present, may be comprised of an insulating material such as $SiO_2$, $SiN_x$ or $AlO_2$, or substantially any other material that may be used as the insulating material of an OLED, which may be deposited by a variety of processes such as plasma enhanced chemical vapor deposition (PECVD), electron beam, etc.

The OLEDs of the present invention have the advantage that they can be fabricated entirely from vacuum-deposited molecular organic materials as distinct, for example, from OLEDs in which some of the layers are comprised of polymeric materials, which cannot be readily deposited using vacuum deposition techniques. A vacuum-deposited material is one which can be deposited in a vacuum typically having a background pressure less than one atmosphere, preferably about $10^{-5}$ to about $10^{-11}$ torr for vacuum deposition, or about 50 torr to about $10^{-5}$ torr for vapor deposition.

Although not limited to the thickness ranges recited herein, the substrate may be as thin as 10μ, if present as a flexible plastic or metal foil substrate, such as aluminum foil, or substantially thicker if present as a rigid, transparent or opaque, substrate or if the substrate is comprised of a silicon-based display driver; the ITO anode layer may be from about 500 Å (1 Å=$10^{-8}$ cm) to greater than about 4000 Å thick; the hole transporting layer from about 50 Å to greater than about 1000 Å thick; the separate emissive layer of a double heterostructure, if present, from about 50 Å to about 200 Å thick; the electron transporting layer from about 50 Å to about 1000 Å thick; and the metal cathode layer from about 50 Å to greater than about 100 Å thick, or substantially thicker if the cathode layer includes a protective silver layer and is opaque.

Thus, while there may be substantial variation in the type, number, thickness and order of the layers that are present, dependent on whether the device includes a single heterostructure or a double heterostructure, whether the device is a SOLED or a single OLED, whether the device is a TOLED or an IOLED, whether the OLED is intended to produce emission in a preferred spectral region, or whether still other design variations are used, the present invention is directed to those devices in which the OLED comprises a heterostructure for producing electroluminescence having a hole transporting layer with a glass structure, where the hole transporting layer comprises a compound having a symmetric molecular structure, and the end groups of the symmetric molecule are hole transporting amine moieties having an unsaturated linkage between two arenes. The compound may be substantially the only component of the hole transporting layer, may be the predominant component in a hole transporting layer that is doped with other materials, or may be a dopant in the hole transporting layer. The hole transporting layer may be emissive, for example in a single heterostructure OLED having an emissive hole transporting layer, or may be non-emissive.

The subject invention as disclosed herein may be used in conjunction with co-pending applications: "High Reliability, High Efficiency, Integratable Organic Light Emitting Devices and Methods of Producing Same", Ser. No. 08/774,119 (filed Dec. 23, 1996), now U.S. Pat. No. 6,046,543; "Novel Materials for Multicolor LED's", Ser. No. 08/850,264 (filed May 2, 1997), now U.S. Pat. No. 6,045,930; "Electron Transporting and Light Emitting Layers Based on Organic Free Radicals", Ser. No. 08/774,120 (filed Dec. 23, 1996), now U.S. Pat. No. 5,811,833; "Multicolor Display Devices", Ser. No. 08/772,333 (filed Dec. 23, 1996), now U.S. Patent No. 6,013,982; "Red-Emitting Organic Light Emitting Devices (LED's)", Ser. No. 08/774,087 (filed Dec. 23, 1996), now U.S. Pat. No. 6,048,630; "Driving Circuit For Stacked Organic Light Emitting Devices", Ser. No. 08/792,050 (filed Feb. 3, 1997), now U.S. Pat. No. 5,757,139; "High Efficiency Organic Light Emitting Device Structures", Ser. No. 08/772,332 (filed Dec. 23, 1996), now U.S. Pat. No. 5,834,893; "Vacuum Deposited, Non-Polymeric Flexible Organic Light Emitting Devices", Ser. No. 08/789,319 (filed Jan. 23, 1997), now U.S. Pat. No. 5,844,363; "Displays Having Mesa Pixel Configuration", Ser. No. 08/794,595 (filed Feb. 3, 1997), now U.S. Pat. No. 6,091,195; "Stacked Organic Light Emitting Devices", Ser. No. 08/792,046 (filed Feb. 3, 1997), now U.S. Pat. No. 5,917,280; "High Contrast Transparent Organic Light Emitting Device Display", Ser. No. 08/821,380 (filed Mar. 20, 1997), now U.S. Pat. No. 5,986,401; "Organic Light Emitting Devices Containing A Metal Complex of 5-Hydroxy-Quinoxaline as A Host Material", Ser. No. 08/838,099 (filed Apr. 15, 1997), now U.S. Pat. No. 5,861,219; "Light Emitting Devices Having High Brightness", Ser. No. 08/844,353 (filed Apr. 18, 1997), now U.S. Pat. No. 6,125,226; "Organic Semiconductor Laser", Provisional Serial No. 60/046,061 (filed May 9, 1997), "Organic Semiconductor Laser", Ser. No. 08/859,468 (filed May 19, 1997), now U.S. Pat. No. 6,111,902; "Saturated Full Color Stacked Organic Light Emitting Devices", Ser. No. 08/858,994 (filed May 20, 1997), now U.S. Pat. No. 5,932,895; "An Organic Light Emitting Device Containing a Hole Injection Enhancement Layer", Ser. No. 08/865,491 (filed May 29, 1997), now U.S. Pat. No. 5,998,803; "Plasma Treatment of Conductive Layers", Ser. No. PCT/US97/10252; (filed Jun. 12, 1997); "Patterning of Thin Films for the Fabrication of Organic Multi-Color Displays", Ser. No. 09/202,152 (filed Jun. 14, 1999), now U.S. Pat. No. 6,259,202; "Double Heterostructure Infrared and Vertical Cavity Surface Emitting Organic Lasers", Ser. No. 60/053,176 (filed Jul. 18, 1997); "Oleds Containing Thermally Stable Asymmetric Charge Carrier Materials", Ser. No. 08/925,029 (filed Sep. 8, 1997), now U.S. Pat. No. 6,242,115; "Light Emitting Device with Stack of Oleds and Phosphor Downconverter", Ser. No. 08/925,403 (filed Sep. 9, 1997), now U.S. Pat. No. 5,874,803; "An Improved Method for Depositing Indium Tin Oxide Layers in Organic Light Emitting Devices", Ser. No. 08/928,800 (filed Sep. 12, 1997), now U.S. Pat. No. 5,981,306; "Azlactone-Related Dopants in the Emissive Layer of an OLED", Ser. No. 08/948,130 (filed Oct. 9, 1997), now U.S. Pat. No. 6,030,715; "A Highly Transparent Organic Light Emitting Device Employing a Non-Metallic Cathode", Ser. No. 08/964,863 (filed Nov. 5, 1997); "Low Pressure Vapor Phase Deposition of Organic Thin Films", Ser. No. 08/972,156 (filed Nov. 17, 1997); "Method of Fabricating and Patterning OLEDS", Ser. No. 08/977,205 (filed Nov. 24, 1997) now U.S. Pat. No. 6,013,538; "Method for Deposition and Patterning of Organic Thin Film", Ser. No. 08/976,666 (filed Nov. 24, 1997), now U.S. Pat. No. 5,953,587; "OLEDs Doped with Phosphorescent Compounds", Ser. No. 08/980,986 (filed Dec. 1, 1997), now U.S. Pat. No. 6,303,238; "Organic Vertical-Cavity Surface-Emitting Laser Confirmation", Ser. No. 09/010,594 (filed Jan. 22, 1998), now U.S. Pat. No. 6,160,828; "Electron Transporting and Light Emitting Layers Based on Organic Free Radicals", Ser. No. 09/025,660 (filed Feb. 18, 1998), now U.S. Pat. No. 5,922,396; "Method of Making a Display", Ser. No. 09/050,084 (filed Mar. 30, 1998), now U.S. Pat. No. 6,245,393; "Aluminum Complexes Bearing Both Electron Transporting and Hole Transporting Moieties", Ser. No. 09/053,030 (filed Apr. 1, 1998); "Highly Transparent Non-Metallic Cathodes", Ser. No. 09/054,707 (filed Apr. 3, 1998); and "Color-Tunable Oganic Light Emitting Devices", Ser. No. 09/058,142 (filed Apr. 10, 1998), now U.S. Pat. No. 6,287,712; each co-pending application being incorporated herein by reference in its entirety. The subject invention may also be used in conjunction with the subject matter of each of co-pending U.S. patent application Ser. Nos. 08/354,674 (now U.S. Pat. No. 5,981,306), 08/613,207 (now U.S. Pat. No. 5,703,436), 08/632,322 (now U.S. Pat. No. 5,757,026) and 08/693,359 and provisional patent application Serial Nos. 60/010,013 (now U.S. Pat. No. 5,986,268), 60/024,001 (now U.S. Pat. No. 5,844,363) and 60/025,501 (now U.S. Pat. No. 6,125,226), each of which is also incorporated herein by reference in its entirety.

OLEDS of the present invention may be fabricated using the materials and structures as disclosed in these co-pending applications.

It has been shown in co-pending application "OLEDs Containing Thermally Stable asymmetric Charge Carrier Materials", Ser. No. 08/925,029 (filed Sep. 8, 1997), now U.S. Pat. No. 6,242,115, which is incorporated herein by reference in its entirety, that charge carrier materials having an asymmetric molecular structure may have a high $T_g$ and be suitable for use in an OLED. It has also been shown in that application that β-NPD may be suitable for use as a charge carrier material in an OLED. OLEDS of the present invention may be fabricated using the materials and structures as disclosed in this co-pending application.

The OLED of the present invention may be used in substantially any type of device which is comprised of em OLED, for example, in OLEDs that are incorporated into a larger display, a vehicle, a computer, a television, a printer, a large area wall, theater or stadium screen, a billboard or a sign.

This invention will now be described in detail with respect to showing how certain specific representative embodiments thereof can be made, the materials, apparatus and process steps being understood as examples that are intended to be illustrative only. In particular, the invention is not intended to be limited to the methods, materials, conditions, process parameters, apparatus and the like specifically recited herein.

Procedures for Fabrication of Organic Light-Emitting Devices (OLEDs)

Chemicals

ISB was prepared according to the following procedure: A round bottom flask was charged with Na-t-butoxicle (4.25 g), $Pd_2dba_3$ (0.22 g), DPPF (diphenylphosphinoferrocene 0.33 g), and 50 ml anhydrous toluene. The reaction mixture was stirred under argon at 90° C. for 15 minutes. Then dibromobiphenyl (3.12 g) and iminostilbene (4.25 g) were added, and the reaction was stirred for 8 hours until the amine could not be detected by mass spectroscopy. The solvent was then stripped from the reaction mixture and the crude residue was dried under vacuum. The dried residue was then subjected to a gradient sublimation under reduced pressure ($10^{-4}$ torr). The sublimation yielded 2.06 g of pure material, 36% of the theoretical reaction yield.

IDB was prepared according to the following procedure: 51 mmol (10.000 g) iminodibenzyl was reacted with 17 mmol (6.94 g) 4,4'-diiodobiphenyl. The reaction product was added to a round bottom flask fitted with a condenser, along with 34 mmol (2.16 g) copper powder, 68 mmol (9.398 g) potassium carbonate, 2 mmol (0.530 g) 18-crown-6 ether, and 20 ml o-dichlorobenzene. The flask was heated to 185° C. and then refluxed under argon for 24 hours. The reaction mixture was filtered hot and the filtrate was put under vacuum to remove the solvent. The residue was then passed through a short column of silica gel in toluene. The solvent was then removed from the column filtrate and the solid left behind was sublimed at 220° C. under a vacuum of 0.01 Torr. for purification.

The electron transporting material $Alq_3$, as well as the TPD and NPD, were synthesized according to literature procedure. All organic materials were sublimed before use.

The fluorene bridged materials were prepared according to the following general procedure: A round bottomed flask was charged with $Pd_2dba_3$ (0.030 eq), dppf (0.045 eq), and Na-t-butoxide (3.0 eq) in a nitrogen glove box. Anhydrous toluene was added and the reaction was stirred for 15 minutes. The 2,7-dibromofluorene (1.0 eq) was added against a stream of nitrogen and the reaction and the reaction was stirred for another 15 minutes. Following the addition of diarylamine (3–5 eq), the mixture was heated to reflux for 8–24 hours. The progress of the reaction was monitored by TLC (hexane or hexane/ethyl acetate) and/or by mass spectroscopy until no more diarylamine could be detected. The reaction mixture was concentrated to dryness under reduced pressure, dissolved in minimal $CHCl_3$, and recrystallized with ethanol or hexanes. The product was further purified by gradient sublimation under reduced pressure.

TPF was synthesized using 2,7-dibromofluorene and tolylphenyl amine according to the general procedure, yielding 2.65 g (25%).

NPF was synthesized using 2,7-dibromofluorene and phenyl-1-naphthyl amine according to the general procedure, yielding 2.21 g (29%).

ISF was synthesized using 2,7-dibromofluorene and iminostilbene according to the general procedure, yielding 3.5 g (35%).

Procedures

ITO/Borosilicate substrates (100 Ω/square) were cleaned by sonicating with detergent for five minutes followed by rinsing with deionized water. They were then treated twice in boiling 1,1,1-trichloroethane, for two minutes. The substrates were then sonicated twice with acetone for two minutes and twice with methanol for two minutes.

The background pressure prior to deposition was $8 \times 10^{-7}$ torr and the pressure during the deposition was around $5 \times 10^{-7}$ to $2 \times 10^{-6}$ torr.

The chemicals were sublimed from resistively heated tantalum boats, and then deposited at a rate from 1 to 3.6 Å/s. The thickness was controlled at 300 Å.

The electron transporting layer ($Alq_3$) was deposited at a rate between 1 to 3.3 Å/s. The total thickness of this layer was controlled at 450 Å.

The substrates were then released to air and masks were put directly on the substrates. The masks are made of stainless steel sheet and contain holes with diameters of 0.25, 0.5, 0.75, and 1.0 mm. The substrates were then put back into vacuum for further coating.

Magnesium and silver were co-deposited at a rate of 2 Å/s. The ratio of Mg:Ag was 9:1. The thickness of this layer was 500 Å. Finally, 1000 Å Ag was deposited at the rate of 2.7 Å/s.

Characteristics of the Devices

Figure 2:
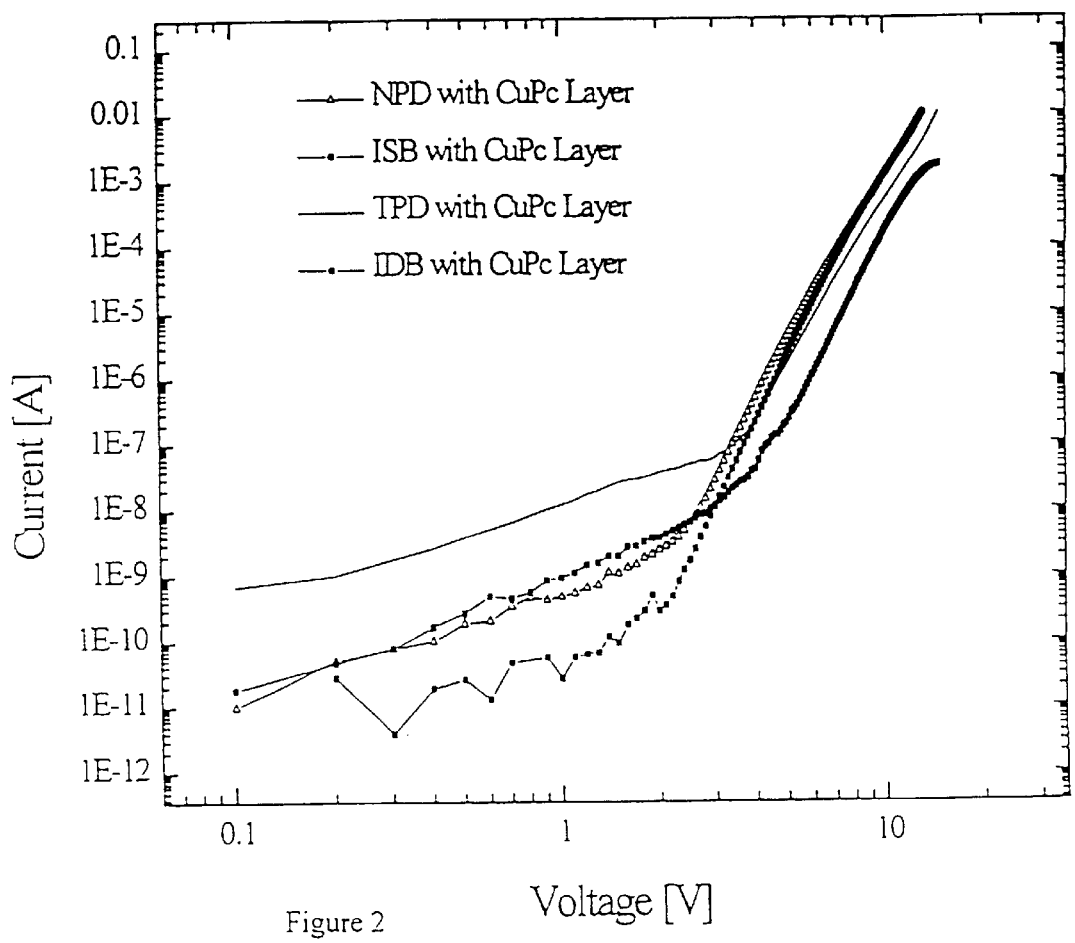
FIG. 2 shows a plot of current v. voltage for an embodiment of the present invention having a CuPc hole injection enhancement layer.

The devices were characterized within one day of fabrication. The current-voltage (I–V) characteristics for the devices having a biphenyl bridged material as the HTL are shown in FIGS. 1 and 2. I–V curves, quantum yields, and luminance were measured. OLED data derived from these measured quantities are tabulated in Table 2.

FIG. 1 shows the current-voltage characteristics of OLEDs having a single heterostructure comprising: an ITO anode, an HTL, an $Alq_3$ ETL, and an Mg—Ag cathode, deposited sequentially on a substrate, as discussed above. Four different plots are shown for four different HTL materials: TPD, NPD, ISB and IDB. The current-voltage plots for TPD, NPD and ISB are very similar, showing that the current-voltage characteristics of the OLED do not significantly change, regardless of whether the HTL is TPD, NPD or ISB. The current-voltage plot for IDB shows a lower current than the plots for TPD, NPD and ISB, indicating that IDB may be a less desirable HTL from the perspective of current-voltage characteristics.

FIG. 2 shows the current-voltage characteristics of OLEDs having a single heterostructure with a hole injection enhancement layer, comprising: an ITO anode, a CuPc hole injection enhancement layer, an HTL, an $Alq_3$ ETL, and an Mg—Ag cathode, deposited sequentially on a substrate, as discussed above. Four different plots are shown for four different HTL materials: TPD, NPD, ISB and IDB. The current-voltage plots for TPD, NPD and ISB are very similar, showing that the current-voltage characteristics of the OLED do not significantly change, regardless of whether the HTL is TPD, NPD or ISB. The current-voltage plot for IDB shows a lower current than the plots for TPD, NPD and ISB, indicating that IDB may be a less desirable HTL from the perspective of current-voltage characteristics.

FIGS. 1 and 2 show that OLEDs using ISB as the HTL can have current-voltage characteristics similar to those of OLEDs using TPD or NPD as the HTL, for two different OLED configurations. This similarity, in conjunction with the higher $T_g$ of ISB and the longer expected lifetimes of OLEDs using ISB, indicate that ISB is a superior HTL.

The device data represented in FIGS. 3–7 were obtained from devices where the hole transporting layers were held constant at 400 Å. Therefore when the intermediate later of 50 Å of NPD was used, the fluorene layer was held to 350 Å. The standard consisted of a NPD layer of 400 Å. After depositing the HTL, 500 Å of Alq$_3$ was deposited for the emission layer. Magnesium/Silver (10:1) cathodes, 500 Å, were deposited prior to a 100 Å silver cap. In these devices we see emission exclusively from the Alq$_3$ layer.

Figure 3:
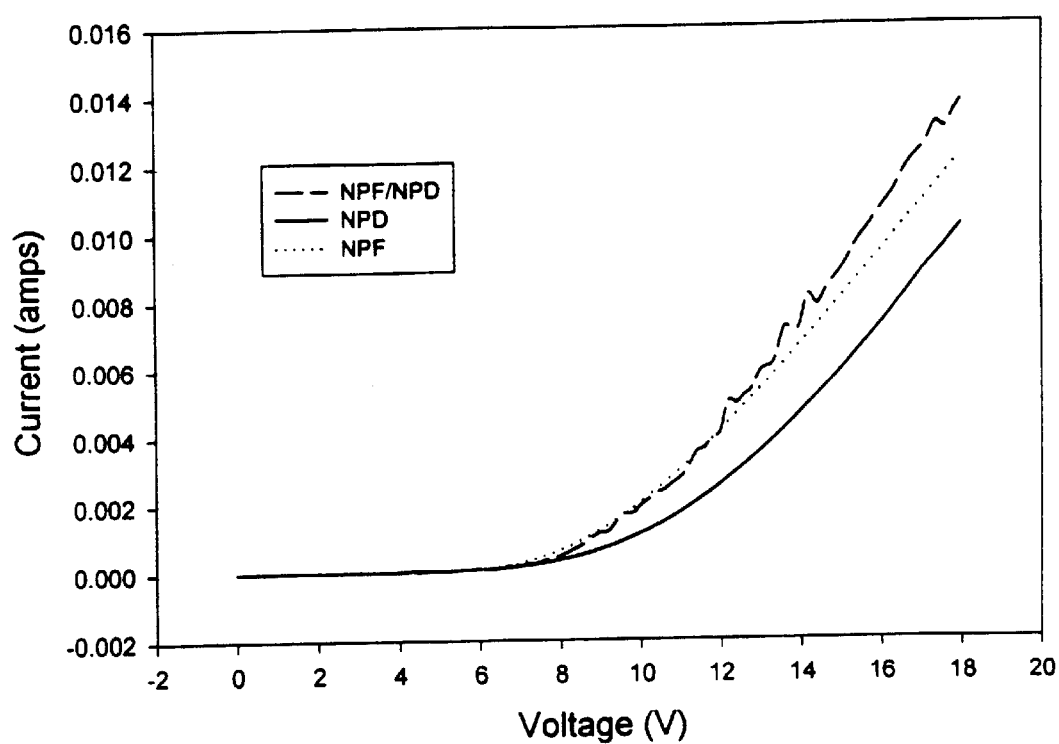
FIG. 3 shows plots of current v. voltage for OLEDs having an HTL comprised of NPF, NPF/NPD or NPD.

FIG. 3 shows the current-voltage characteristics of NPF/NPD and NPF devices constructed according to the architecture described above. Three different plots are shown for the three different HTL materials, NPF/NPD, NPF, and NPD (standard). FIG. 3 shows that the current-voltage characteristics of NPF and NPF/NPD devices are nearly the same as the standard NPD device. There is actually a lower turn on voltage for the device containing the NPF as the HTL.

Figure 4:
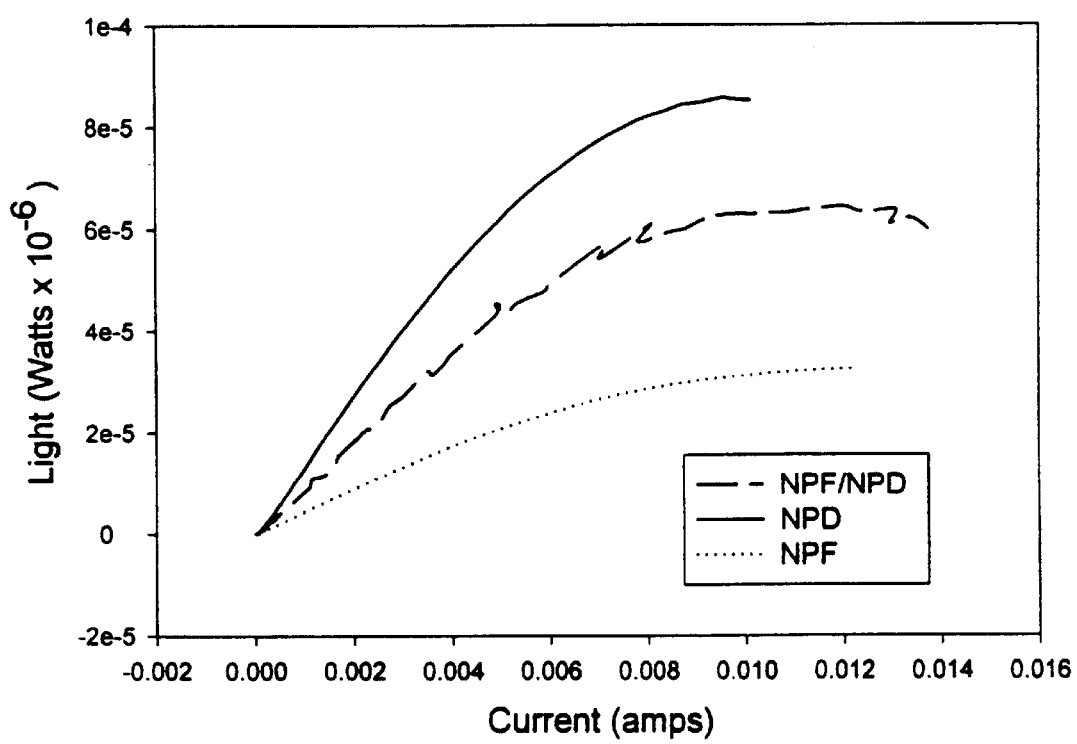
FIG. 4 shows plots of brightness v. current for OLEDs having an HTL comprised of NPF, NPF/NPD or NPD.

FIG. 4 shows the brightness-current characteristics of NPF/NPD, NPF, and NPD devices constructed according to the architecture described above. Three different plots are shown for the three different HTL materials, NPF/NPD, NPF, and NPD (standard). FIG. 4 shows that the NPF devices are not as bright (lower quantum efficiency) than the standard NPD device.

Figure 5:
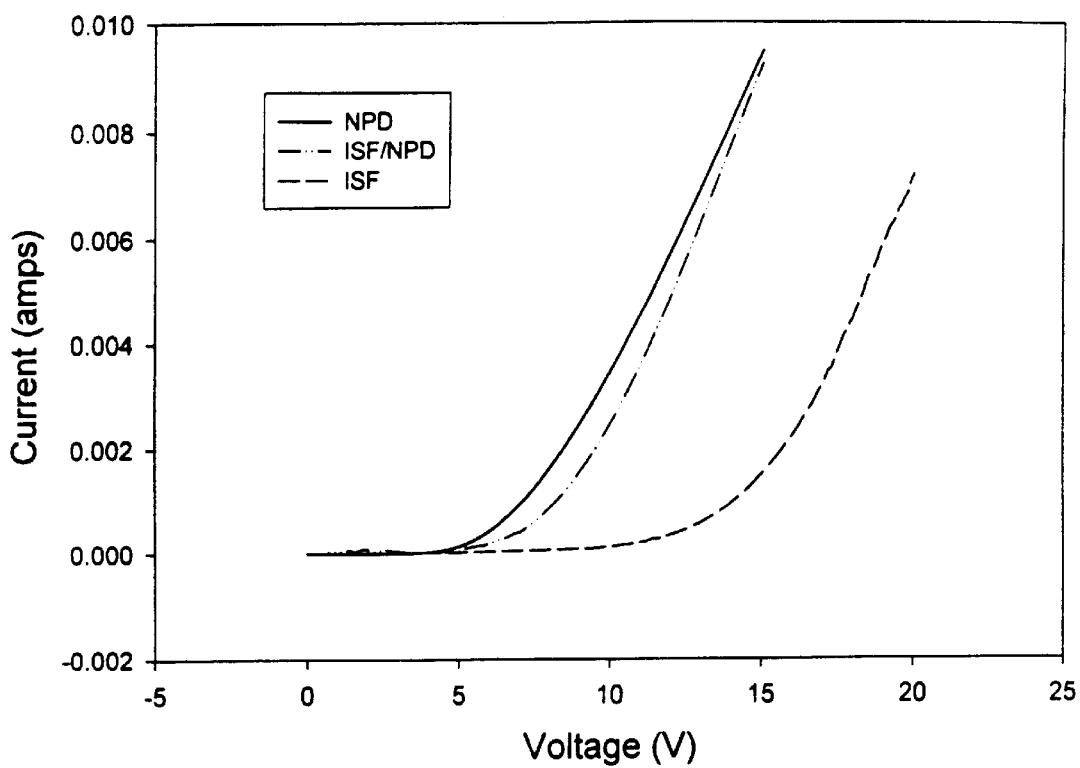
FIG. 5 shows plots of current v. voltage for OLEDs having an HTL comprised of ISF, ISF/NPD or NPD.

FIG. 5 shows the current-voltage characteristics of ISF/NPD and ISF devices constructed according to the architecture described above. Three different plots are shown for the three different HTL materials, ISF/NPD, ISF, and NPD (standard). FIG. 5 shows that the current-voltage characteristics of ISF/NPD devices are comparable to the standard NPD devices. Using only ISF as the HTL leads to a high turn-on voltage resulting from a large energy barrier at the HTL/ETL interface. The use of a 50 Å NPD layer facilitates the injection of holes into the Alq$_3$ emissive layer. From the relative energy levels of the two HTL's, it can be deduced that ISF is a better match with ITO, while NPD is a better match with Alq$_3$, and thus needed within the device architecture.

Figure 6:
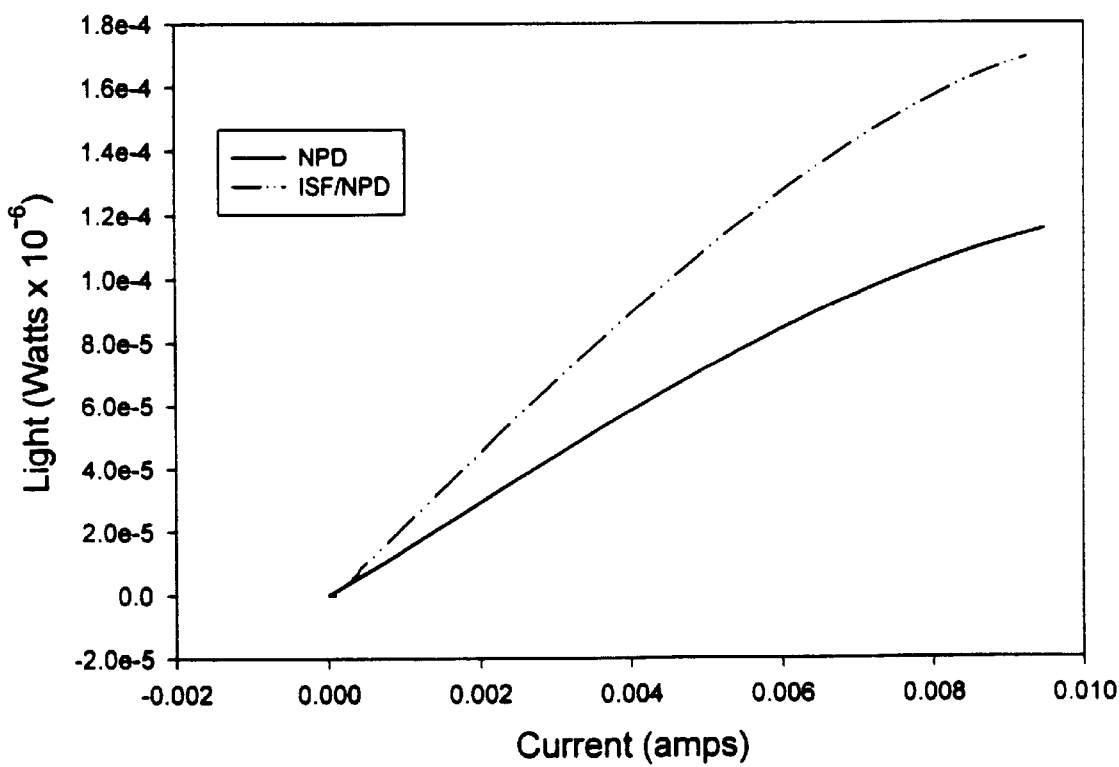
FIG. 6 shows plots of brightness v. current for OLEDs having an HTL comprised of ISF/NPD or NPD.

FIG. 6 shows the brightness-current characteristics of the ISF/NPD device constructed according to the architecture described above. Two different plots are shown for the two different HTL materials, ISF/NPD and NPD (standard). FIG. 6 shows that the ISF/NPD device yields a greater quantum efficiency than the standard NPD device. The quantum efficiency of the pure ISF device was very poor, showing a flat line on this scale.

In order to test the temperature effects on the device operation, devices where placed in a heating source under a nitrogen atmosphere, and heated at a constant rate, while a constant current was applied. FIG. 7 shows the temperature-voltage behavior of the NPD, NPF/NPD, and ISF/NPD devices constructed according to the architecture described above. Three different plots are shown for the three different HTL materials, NPD, NPF/NPD, and ISF/NPD. A sharp drop in voltage indicates the temperature at which the device fails. The behavior of the pure NPD devices consistently shows a sharp drop in voltage at 105–108° C. The NPF/NPD devices show a sharp drop in voltage near 120° C. The ISF/NPD devices show a sharp drop in voltage at 170° C. In all cases the temperature at which failure occurs is slightly above the glass transition temperature for the HTL material. Even though a NPD layer is used in the NPF/NPD and ISF/NPD devices, the minimal amount does not seem to affect the thermal stability of the architecture. This could possibly point to de-wetting of the HTL from the ISO as the cause of the device failure.

What is claimed is:

1. An organic light emitting device comprising a heterostructure for producing electroluminescence, wherein the heterostructure comprises a substrate;

an anode layer;

a hole transporting layer having a glass structure, and wherein the hole transporting layer comprises a compound of the formula:

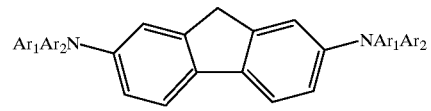

wherein Ar$_1$ and Ar$_2$ are substituted or unsubstituted arene moieties, with the proviso that Ar$_1$ and Ar$_2$ are different and at least one of Ar$_1$ and Ar$_2$ is unsubstituted, or

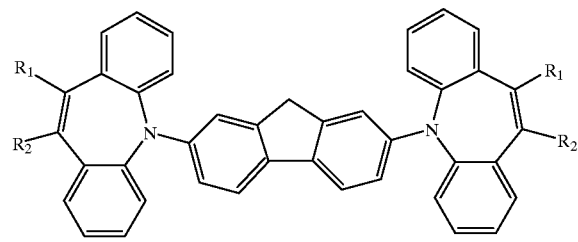

wherein R$_1$ and R$_2$ are, independently of one another, selected from the group consisting of hydrogen, an alkyl group, a phenyl group, a substituted alkyl group and a substituted phenyl group, and wherein R$_1$ and R$_2$ may be bridged;

an electron transporting layer; and a cathode layer.

2. An organic light emitting device of claim 1, wherein the compound has the formula:

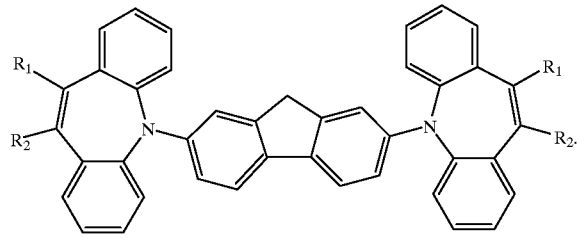

3. An organic light emitting device of claim 2, wherein the R$_1$ and R$_2$ are the same.

4. An organic light emitting device of claim 2, wherein the R$_1$ and R$_2$ are different.

5. An organic light emitting device of claim 1, wherein the compound has the formula:

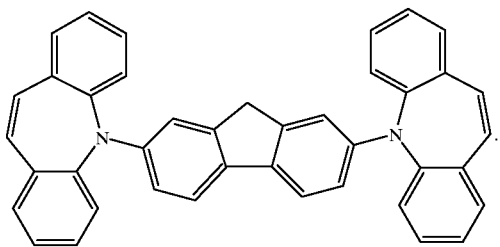

6. An organic light emitting device of claim 1, wherein the compound has the formula:

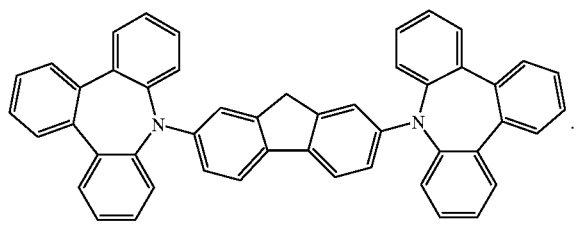

7. An organic light emitting device of claim 1, wherein the compound has the formula:

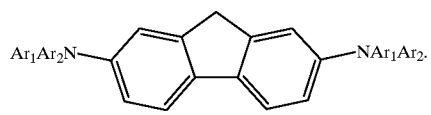

8. An organic light emitting device of claim 1, wherein the compound has the formula:

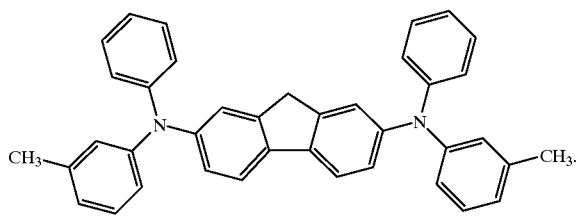

9. An organic light emitting device of claim 1, wherein the compound has the formula:

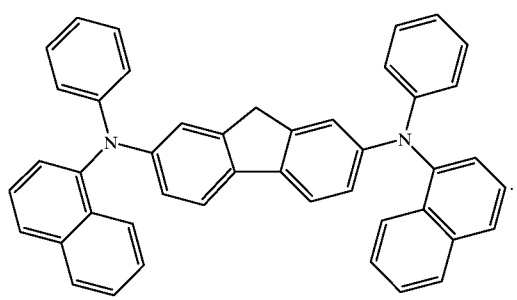

10. An organic light emitting device of claim 1, wherein the compound has the formula:

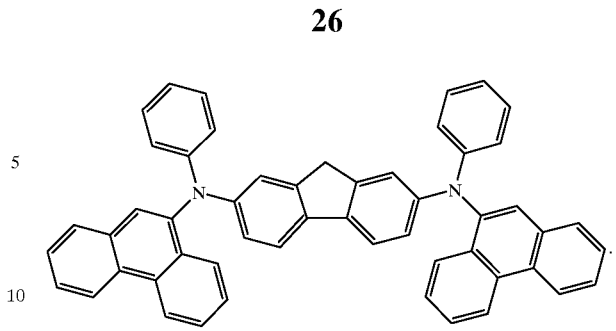

11. An organic light emitting device comprising a heterostructure for producing electroluminescence, wherein the heterostructure comprises
   a substrate;
   an anode layer;
   a hole transporting layer having a glass structure, wherein the hole transporting layer comprises a compound of the formula:

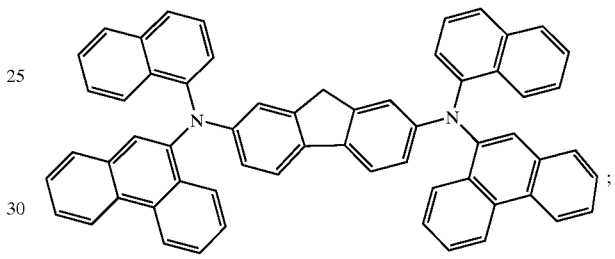

an electron transporting layer; and
   a cathode layer.

12. The organic light emitting device of claim 1, wherein the compound is the predominant component in the hole transporting layer.

13. The organic light emitting device of claim 1, wherein the compound is a dopant in the hole transporting layer.

14. The organic light emitting device of claim 1 wherein the heterostructure for producing electroluminescence comprises, in sequence, the substrate, the cathode layer, the electron transporting layer, the hole transporting layer and the anode layer.

15. The organic light emitting device of claim 1 wherein the heterostructure for producing electroluminescence comprises, in sequence, the substrate, the cathode layer, the electron transporting layer, the hole transporting layer, a hole injector layer and the anode layer.

16. The organic light emitting device of claim 1 wherein the heterostructure for producing electroluminescence comprises, in sequence, the substrate, the cathode layer, the electron transporting layer, an emissive layer, the hole transporting layer and the anode layer.

17. The organic light emitting device of claim 1 wherein the heterostructure for producing electroluminescence comprises, in sequence, the substrate, the cathode layer, the electron transporting layer, an emissive layer, the hole transporting layer, a hole injector layer and the anode layer.

18. The organic light emitting device of claim 1 wherein the heterostructure for producing electroluminescence comprises, in sequence, the substrate, the anode layer, the hole transporting layer, the electron transporting layer, and the cathode layer.

19. A display incorporating the organic light emitting device of claim 1.

20. A vehicle incorporating the organic light emitting device of claim 1.

21. A computer incorporating the organic light emitting device of claim 1.

22. A television incorporating the organic light emitting device of claim 1.

23. A printer incorporating the organic light emitting device of claim 1.

24. A wall, theater or stadium screen incorporating the organic light emitting device of claim 1.

25. A billboard or a sign incorporating the organic light emitting device of claim 1.

26. A compound of the formula:

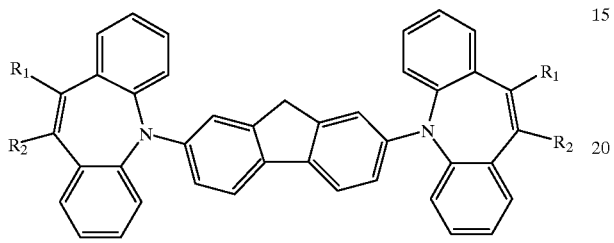

wherein $R_1$ and $R_2$ are, independently of one another, selected from the group consisting of hydrogen, an alkyl group, a phenyl group, a substituted alkyl group and a substituted phenyl group, and wherein $R_1$ and $R_2$ may be bridged.

27. A compound of claim 26, wherein the $R_1$ and $R_2$ are the same.

28. A compound of claim 26, wherein the $R_1$ and $R_2$ are different.

29. A compound of claim 26, wherein the compound has the formula:

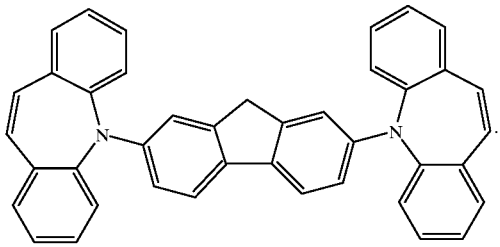

30. A compound of claim 26, wherein the compound has the formula:

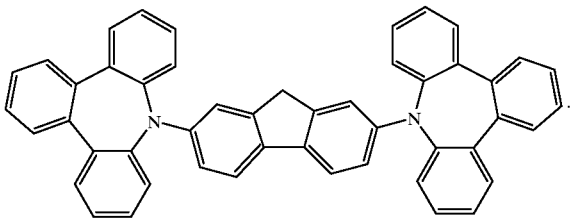

31. A compound of the formula:

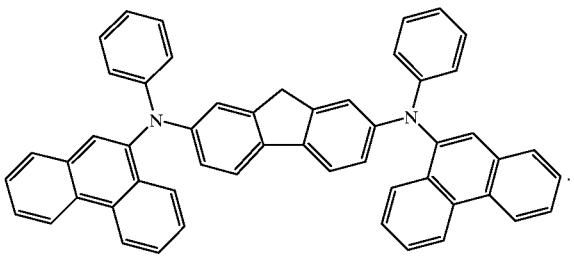

32. A compound of the formula:

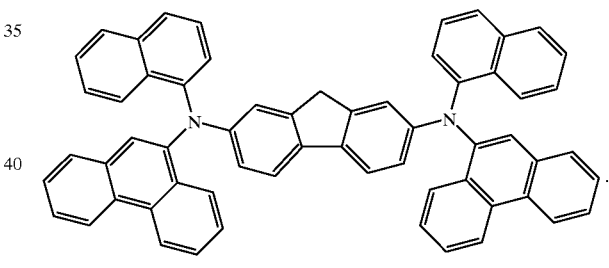

* * * * *

UNITED STATES PATENT AND TRADEMARK OFFICE
CERTIFICATE OF CORRECTION

PATENT NO. : 6,387,544 B1
DATED : May 14, 2002
INVENTOR(S) : Thompson et al.

It is certified that error appears in the above-identified patent and that said Letters Patent is hereby corrected as shown below:

Column 6,
Line 55, change "nattached" to -- unattached --;

Column 7,
Line 17, change "b,e" to -- be --; and

Column 20,
Line 46, change "asymmetric" to -- Asymmetric --.

Signed and Sealed this

Fifteenth Day of October, 2002

Attest:

JAMES E. ROGAN
Attesting Officer    Director of the United States Patent and Trademark Office